United States Patent
Chang et al.

(10) Patent No.: US 12,188,049 B2
(45) Date of Patent: Jan. 7, 2025

(54) METHODS FOR MOBILIZING STEM CELLS

(71) Applicant: TZU CHI UNIVERSITY, Hualien (TW)

(72) Inventors: Hsin-Hou Chang, Hualien (TW); Der-Shan Sun, Hualien (TW)

(73) Assignee: TZU CHI UNIVERSITY, Hualien (TW)

(*) Notice: Subject to any disclaimer, the term of this patent is extended or adjusted under 35 U.S.C. 154(b) by 458 days.

(21) Appl. No.: 16/848,065

(22) Filed: Apr. 14, 2020

(65) Prior Publication Data

US 2021/0317414 A1    Oct. 14, 2021

(51) Int. Cl.
*C12N 5/0775* (2010.01)
*A61K 38/17* (2006.01)
*A61K 47/69* (2017.01)

(52) U.S. Cl.
CPC .......... *C12N 5/0663* (2013.01); *A61K 38/178* (2013.01); *A61K 47/6911* (2017.08)

(58) Field of Classification Search
None
See application file for complete search history.

(56) References Cited

FOREIGN PATENT DOCUMENTS

| CN | 105431521 A | 3/2016 |
|---|---|---|
| CN | 106687581 A | 5/2017 |
| WO | 2004094619 A2 | 11/2004 |
| WO | 2008036374 A2 | 3/2008 |

OTHER PUBLICATIONS

The Merck Manual (https://www.merckmanuals.com/professional/gastrointestinal-disorders/irritable-bowel-syndrome-ibs/irritable-bowel-syndrome-ibs accessed Nov. 17, 2022).*
Kapupara et al. ("Soluble P-selectin promotes retinal ganglion cell survival through activation of Nrf2 signaling after ischemia injury" Cell Death and Disease, (2017) 8, e3172).*
Shima et al. ("Neuroprotective effects of Granulocyte Colony Stimulating Factor on Ischemia-Reperfusion Injury of the Retina" Ophthalmic Res 2012;48:199-207).*
Sun et al. ("Soluble P-selectin rescues mice from anthrax lethal toxin-induced mortality through PSGL-1 pathway mediated correction of hemostasis" Virulence, 2017; vol. 8 (7), 1216-1228).*
Knobler et al. ("TNF-alpha, chronic hepatitis C and diabetes, a novel triad" Abstract; QJM. Jan. 2005; 98(1): 1-6).*
Carreno et al. ("Randomized controlled trial of recombinant human granulocyte macrophage colony stimulating factor for the treatment of chronic hepatitis C" Cytokine, vol. 12, No. 2 (Feb. 2000; pp. 165-170).*
Irby et al. (Lipid-Drug Conjugate for Enhancing drug delivery Mol. Pharmaceutics, 2017, 14, 1325-1338).*
Official Action issued in Taiwan Patent Application No. 109112546 on Feb. 20, 2021.
Search Report issued in Taiwan Patent Application No. 109112546 on Feb. 20, 2021. English translation attached.
Blann, A et al: "The adhesion molecule P-selectin and cardiovascular disease", Eur Heart J. Dec. 2003;24(24):2166-79.
Frenette, Paul S et al: "Sulfated glycans induce rapid hematopoietic progenitor cell mobilization: Evidnce for selectin-dependent and independent mechanisms", Blood. Oct. 1, 2000;96(7):2460-8.
Nadar S K et al: "Platelet indexes in relation to target organ damage in high-risk hypertensive patients—A substudy of the Anglo-Scadinavian Cardiac Outcomes Trail (ASCOT)", J Am Coll Cardiol. Jul. 21, 2004;44(2):415-22.
Search Report issued in European Patent Application No. 21164662.5 on Sep. 22, 2021.
Cao, Xingyu et al, Development of mesenchymal stem cells homing. Clinical medicine, Mar. 2013, vol. 33, No. 3, pp. 111-114 (with Abstract translation).
Frenette, Paul S. et al., "Sulfated glycans induce rapid hematopoietic progenitor cell mobilization: evidence for selectin-dependent and independent mechanisms," Blood, Oct. 2000, vol. 96, No. 7, pp. 2460-2468.
Office Action with Search Report issued on Jan. 17, 2024 in Chinese patent application No. 202110386392.X. English translation of search report included.

* cited by examiner

*Primary Examiner* — Julie Ha
*Assistant Examiner* — Tara L Martinez
(74) *Attorney, Agent, or Firm* — Prosyla Group PC (57) ABSTRACT

The present disclosure provides a soluble P-selectin (sP-sel) interfering the interaction between stem cells and niches to mobilize stem cells from bone marrow. The mobilization of stem cells with sP-sel can treat a subject in need of preservation, repair, or regeneration of a tissue, or revascularization.

6 Claims, 7 Drawing Sheets

METHODS FOR MOBILIZING STEM CELLS

FIELD OF THE INVENTION

The present disclosure relates generally to methods for inducing mobilization of stem cells for wound healing and/or tissue regeneration applications by administration of a soluble P-selectin.

BACKGROUND OF THE INVENTION

Stem cells (SCs) are defined as cells with the unique capacity to self-replicate throughout the entire life of an organism and to differentiate into various cell types of the body. Two well-known types of stem cells are embryonic stem cells and adult stem cells. Since stem cells are capable of differentiating into a broad variety of cell types, they play an important role in the wound healing and/or cellular/tissue regenerative processes of various tissues and organs. Some stem cells (such as bone marrow stem cells and hematopoietic stem cells) are released from tissues of origin, and circulate in a subject's circulatory or immune system to migrate into various organs and tissues to become mature, terminally differentiated cells. Therefore, enhancement of stem cell trafficking (i.e., release, circulation, homing and/or migration) can amplify these physiological processes and provide potential therapies for various pathologies.

Mobilization of stem cells from bone marrow into the peripheral blood prior to harvesting is currently being used in allogeneic stem cell transplantation instead of bone marrow in clinical settings. AMD3100, a CXCR4 inhibitor, approved recently for stem cell mobilization induces a more specific mobilization of cells into the circulation than G-CSF via disruption of the CXCR4-SDF1 interaction of bone marrow cells with their microenvironment. For example, US 20180142211 uses CXCR4 antagonistic peptide to mobilize the mesenchymal stem cells to peripheral blood and then obtain the cells.

However, there is still a need to develop an agent for stem cell mobilization.

SUMMARY OF THE INVENTION

The present disclosure provides a method for mobilizing circulating stem cells in a subject, comprising administering to the subject an amount of a soluble P-selectin (sP-sel) effective to mobilize a population of hematopoietic stem cells or progenitor cells for therapeutic applications. In one embodiment, the soluble P-selectin can interfere and/or regulate or modulate the interaction between stem cells and niches.

The present disclosure also provides a method for treating a subject in need thereof of preservation, repair, and/or regeneration of a tissue, and/or revascularization in a subject, comprising administering to the subject an amount of a sP-sel effective to mobilize a population of hematopoietic stem cells or progenitor cells. Enhancement of stem cell trafficking (i.e., release, circulation, homing and/or migration) can amplify these physiological processes and provide therapeutic efficacy for various pathologies.

The present disclosure also provides a method of performing an allogeneic hematopoietic stem cell transplant in a patient in need thereof, the method comprising infusing into the patient a therapeutically effective amount of allogeneic hematopoietic stem cells, wherein the hematopoietic stem cells were mobilized from bone marrow of a human donor into peripheral blood of the human donor by a method comprising administering to the donor an effective amount of a sP-sel.

In one embodiment, the stem cells are hematopoietic cells, progenitor cells or bone marrow stem cells.

In one embodiment, the methods further comprise administering to said subject a second agent prior to, after or concurrently in combination with administering the sP-sel. In a further embodiment, the second agent is selected from the group consisting of G-CSF, GM-CSF, IL-3, GM-CSF/IL-3 fusion proteins, FLK-2/FLT-3 ligand, stem cell factor, IL-6, IL-11, TPO, VEGF, AMD3100 and combinations thereof.

In one embodiment, the amount of the sP-sel ranges from about $10^{-5}$ μg to about 1.5 mg per kg body weight per administration.

In one embodiment, the sP-sel-mobilized circulating stem cells (PselMSCs) can produce stem cell derived-extracellular microvesicle.

In one embodiment, the PselMSCs can ameliorate tissue or organ damage, increase repair, improve glucose tolerance and/or reduce inflammation. In a further embodiment, the tissue damage is a liver damage.

In one embodiment, the PselMSCs can repopulate the bone marrow or hematopoietic stem cell population.

In one embodiment, the PselMSCs can repopulate the bone marrow or hematopoietic stem cell population and rescue tissue injuries, proliferative disorders, inflammatory diseases, immunodeficiency diseases, autoimmune disorders and/or metabolic diseases.

In one embodiment, the sP-sel is a naturally occurring sP-sel or a recombinant sP-sel.

In one embodiment, the sP-sel can further conjugate on a vesicle or liposome.

The present disclosure also provides a method for cell therapy in a subject, comprising administering to the subject an amount of a sP-sel effective to mobilize the stem cells and an amount of stem cells effective to cell therapy. In one embodiment, the sP-sel and the stem cells are administered concurrently, separately or intermittently.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1. Soluble P-selectin but not G-CSF treatments induced mobilization of CD34$^+$ stem cells in mice. Recombinant mouse soluble P-selectin and G-CSF (Filgrastim®) (both 0.1 mg/kg body weight) were intravascular injected twice into 8-week-old experimental male C57Bl/6J mice in a 24 h interval, the blood samples were collected with additional 24 h (A, outline). The levels of circulating CD34+ mononuclear cells were determined using flow cytometry (FC) (A), the vehicle (saline) control groups were normalized to 100% (B).

FIG. 4. Levels of circulating Lin−Sca-1+c-Kit+ (LSK) stem cells after soluble P-selectin stimulation. The LSK hematopoietic stem cells are stem cell lineages capable to repopulate the bone marrow stem cells after lethal γ-irradiation. The experimental outline is illustrated (A). C57BL/6J mice were intravenously injected with soluble P-selectin (0.1 mg/kg) twice daily (n=5). The peripheral blood (PB) was collected and analyzed using flow cytometry (FC) assay right before and 24 hours after the first injection. The absolute numbers of LSK cells in the peripheral blood were quantified (B). Data are reported as the mean±SD. $*P<0.05$, compared with the before experiment groups.

DETAILED DESCRIPTION OF THE INVENTION

Where the definition of terms departs from the commonly used meaning of the term, applicant intends to utilize the definitions provided below, unless specifically indicated otherwise.

As used in this specification and the appended claims, the singular forms "a," "an" and "the" include plural referents unless the content clearly dictates otherwise.

As used herein, the use of "or" means "and/or" unless stated otherwise. In the context of a multiple dependent claim, the use of "or" refers back to more than one preceding independent or dependent claim in the alternative only.

As used herein, the term "one or more" is readily understood by one of skill in the art, particularly when read in context of its usage.

As interchangeably used herein, the terms "individual," "subject," "host," and "patient," refer to a mammal, including, but not limited to, murines (rats, mice), non-human primates, humans, canines, felines, ungulates (e.g., equines, bovines, ovines, porcines, caprines), etc.

As used herein, the term "soluble P-selectin" refers to naturally occurring soluble form of P-selectin and recombinant form thereof, or polymorphic or allelic variant or other isoforms thereof. The term also comprises modified or unmodified soluble P-selectin, such as glycosylated or non-glycosylated forms.

As used herein, the terms "mobilize" and "mobilization" refer to processes by which a population of hematopoietic stem or progenitor cells is released from a stem cell niche.

As used herein, the term "niche" refers to the in vivo or in vitro cellular and molecular microenvironments that regulate stem cell function together with stem cell autonomous mechanisms. This includes control of the balance between quiescence, self-renewal, and differentiation, as well as the engagement of specific programs in response to stress.

As used herein, the term "hematopoietic stem cell" or "HSC" refers to a stem cell that is capable of differentiating into both myeloid lineages (i.e. monocytes, macrophages, neutrophils, basophils, eosinophils, erythrocytes, megakaryocytes/platelets and some dendritic cells) and lymphoid lineages (i.e. T-cells, B-cells, NK-cells, and some dendritic cells).

As used herein, the term "subject" refers to any animal, including mammals, birds, reptiles and amphibians and in preferred embodiments to mammals, including humans, companion animals, food production animals and wild animals.

As used herein, the term "donor" refers to a subject from which one or more cells are isolated prior to administration of the cells, or progeny thereof, into a recipient.

As used herein, the term "effective amount" refers to a quantity of one or more agents, such as a quantity of a soluble P-selectin and/or a second agent described herein that mobilizes a population of hematopoietic stem or progenitor cells upon administration to a subject.

As used herein stem-cell niche (adult or fetal) refers to a microenvironment, within the specific anatomic location where stem cells are found, which interacts with stem cells to regulate cell fate.

Stem cells can produce new cells to repair damage to tissues and therefore have great potential for regenerative medicine. However, they exist in small quantities in tissues and especially in peripheral blood, making it difficult to collect them or use them clinically. Mobilization of stem cells is a way to collect stem cells from bone marrow into the blood. The present disclosure sparingly found that a soluble P-selectin (sP-sel) may interfere in the interaction between stem cells and niches and thus mobilize stem cells from bone marrow. Accordingly, the mobilization of stem cells with sP-sel can treat a subject in need of one or more of preservation, repair, or regeneration of a tissue, or revascularization in the subject.

P-selectin is a member of the selectin family localized in the membranes of α-granules of platelets and the Weibel-Palade bodies (WP bodies) of endothelial cells. P-selectin is expressed as two different forms; one is the "cell-surface" form and the other is the "soluble" form. The former one is expressed on the activated platelet or endothelial cell that is involved in the inflammation of leukocytes and the homing of HSCs. The latter one (i.e., sP-sel) is almost exclusively expressed in the plasma only during the animal/human, which is under stress (e.g. hypoxia) (Chang, H. H. & Sun, D. S. Methods of reducing hypoxic stress in a mammal by administering soluble P-selectin. U.S. Pat. No. 8,377,887 B1 (2012)). A soluble P-selectin molecule, which exists as a monomer in the blood, is 3 kDa smaller than a P-selectin molecule, which exists as an oligomer on a membrane. The soluble P-selectin of healthy individuals originates from the alternatively spliced form found in endothelia cells and platelets. The present invention surprisingly found that treatment of soluble P-selectin may interfere in the interaction between stem cells and niches and thus mobilizes stem cells. The hematopoietic stem and progenitor cells thus mobilized may then be withdrawn from the donor and administered to a patient, where the cells may home to a hematopoietic stem cell niche and re-constitute a population of cells that are damaged or deficient in the patient.

Any forms of sP-sel suitable for mobilization of stem cells can be used in the present disclosure. Examples of the sP-sel of the present disclosure include, but are not limited to, naturally occurring sP-sel and recombinant sP-sel. The sP-sel can be easily obtained by general techniques, such as being isolated from a natural source, purchased from a commercial source, or synthesized with molecular biological techniques. As used herein, exemplary p-selectin may also include in the alternative, platelet alpha-granule membrane protein, CD62, granulocyte membrane protein; GRMP; and/or GMP140.

The sP-sel can be used in combination with a second agent for mobilization of stem cells. Examples of the second agent include, but are not limited to, G-CSF, GM-CSF, IL-3, GM-CSF/IL-3 fusion proteins, FLK-2/FLT-3 ligand, stem cell factor, IL-6, IL-11, TPO, VEGF, AMD3100 and combinations thereof. Preferably, the second agent is G-CSF. The sP-sel and the second agent can be used simultaneously or sequentially.

The sP-sel can be used in combination with stem cells. The sP-sel and the stem cells are administered concurrently, separately or intermittently.

Hematopoietic stem cell transplant therapy can be administered to a subject in need of treatment so as to populate or repopulate one or more blood cell types, such as a blood cell lineage that is deficient or defective in a patient suffering from a stem cell disorder. Hematopoietic stem and progenitor cells exhibit multi-potency, and can thus differentiate into multiple different blood lineages. Hematopoietic stem cells give rise to different types of blood cells, in lines called myeloid and lymphoid. Myeloid and lymphoid lineages both are involved in dendritic cell formation. Myeloid cells include monocytes, macrophages, neutrophils, basophils, eosinophils, erythrocytes, and megakaryocytes to platelets. Lymphoid cells include T cells, B cells, natural killer cells, and innate lymphoid cells.

Hematopoietic stem or progenitor cells mobilized to the peripheral blood of a subject can be withdrawn (e.g., harvested or collected) from the subject by any suitable technique. For example, the hematopoietic stem or progenitor cells may be withdrawn by a blood draw. In some embodiments, hematopoietic stem or progenitor cells mobilized to a subject's peripheral blood as contemplated herein may be harvested (i.e., collected) using apheresis. In some embodiments, apheresis may be used to enrich a donor's blood with mobilized hematopoietic stem or progenitor cells.

The sP-sel disclosed herein can be administered according to various routes of administration, typically by injection, such as local or systemic injection(s). However, other administration routes can be used as well, such as intramuscular, intravenous, intradermal, subcutaneous, etc. For administration, the sP-sel is ordinarily combined with one or more adjuvants appropriate for the indicated route of administration. Furthermore, repeated injections can be performed, if needed. The sP-sel is administered in the range of approximately $10^{-5}$ µg to 1.5 mg per kg body weight.

The sP-sel-mobilized circulating stem cells (PselMSCs) can ameliorate tissue or organ damage, increase repair, improve glucose tolerance and/or reduce inflammation. The PselMSCs also can repopulate the bone marrow or hematopoietic stem cell population and rescue tissue injuries, proliferative disorders, inflammatory diseases, immunodeficiency diseases, genetic disorders, degenerative disorders, autoimmune disorders and/or metabolic diseases. Examples of proliferative disorders include, but are not limited to, hematologic cancer and myeloproliferative disease. Example of immunodeficiency diseases include, but are not limited to, congenital immunodeficiency diseases and acquired immunodeficiency diseases. Example of autoimmune disorders include, but are not limited to, juvenile arthritis, ulcerative colitis, Type 1 diabetes mellitus (Type 1 diabetes), multiple sclerosis (MS), inflammatory bowel disease (IBD), psoriasis, psoriatic arthritis, rheumatoid arthritis (RA), human systemic lupus (SLE), autoimmune lymphoproliferative syndrome (ALPS), and lymphocytic colitis. Example of metabolic diseases include, but are not limited to, glycogen storage diseases, mucopolysaccharidoses, Gaucher's Disease, Hurlers Disease, sphingolipidoses, and metachromatic leukodystrophy.

Withdrawn hematopoietic stem or progenitor cells may be re-infused into the patient, such that the cells may subsequently home hematopoietic tissue and establish productive hematopoiesis, thereby populating or repopulating a line of cells that is defective or deficient in the patient.

Although the invention has been described with reference to preferred embodiments and examples thereof, the scope of the present invention is not limited only to those described embodiments. As will be apparent to persons skilled in the art, modifications and adaptations to the above-described invention can be made without departing from the spirit and scope of the invention, which is defined and circumscribed by the appended claims. The following examples are provided for the intent of illustrating embodiments and advantages of the invention and are not intended to limit its scope.

EXAMPLE

Example 1 Soluble P-Selectin Mediated Mobilization of CD34+ Cells

According to a previous report (Tajima, F., Sato, T, Laver, J. H. & Ogawa, M CD34 expression by murine hematopoietic stem cells mobilized by granulocyte colony-stimulating factor. *Blood* 96, 1989-1993 (2000)), G-CSF-mediated mobilization of mouse CD34+ cells needs 5 doses of injections. Here we showed that on day 3 (after 2 doses of G-CSF injections), there are still no elicitation of circulating CD34+ cells in mice.

Figure 1:
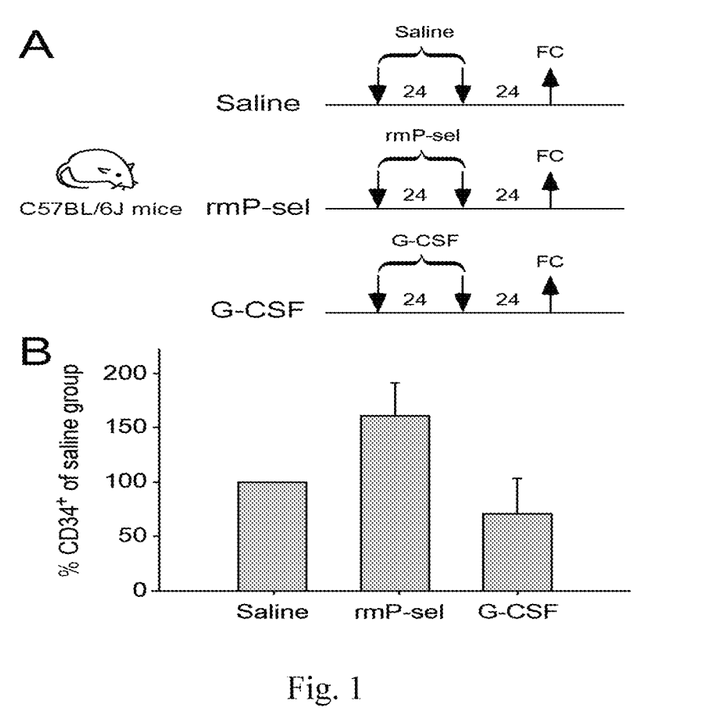

The recombinant mouse P-selectin (rmP-sel) and granulocyte-colony stimulating factor (G-CSF; Filgrastim®) were injected intravenously per treatment (0.1 mg/kg body weigh) to mice. Compared to no induction of circulating CD34+ stem cells previously, the rmP-sel treatments surprisingly and unexpectedly elicited significant amount of CD34+ cells with only 2 injections (see FIG. 1A experimental outline, 1B). These results show that P-selectin is much potent than G-CSF on the mobilization of circulating CD34+ cells.

Figure 2:
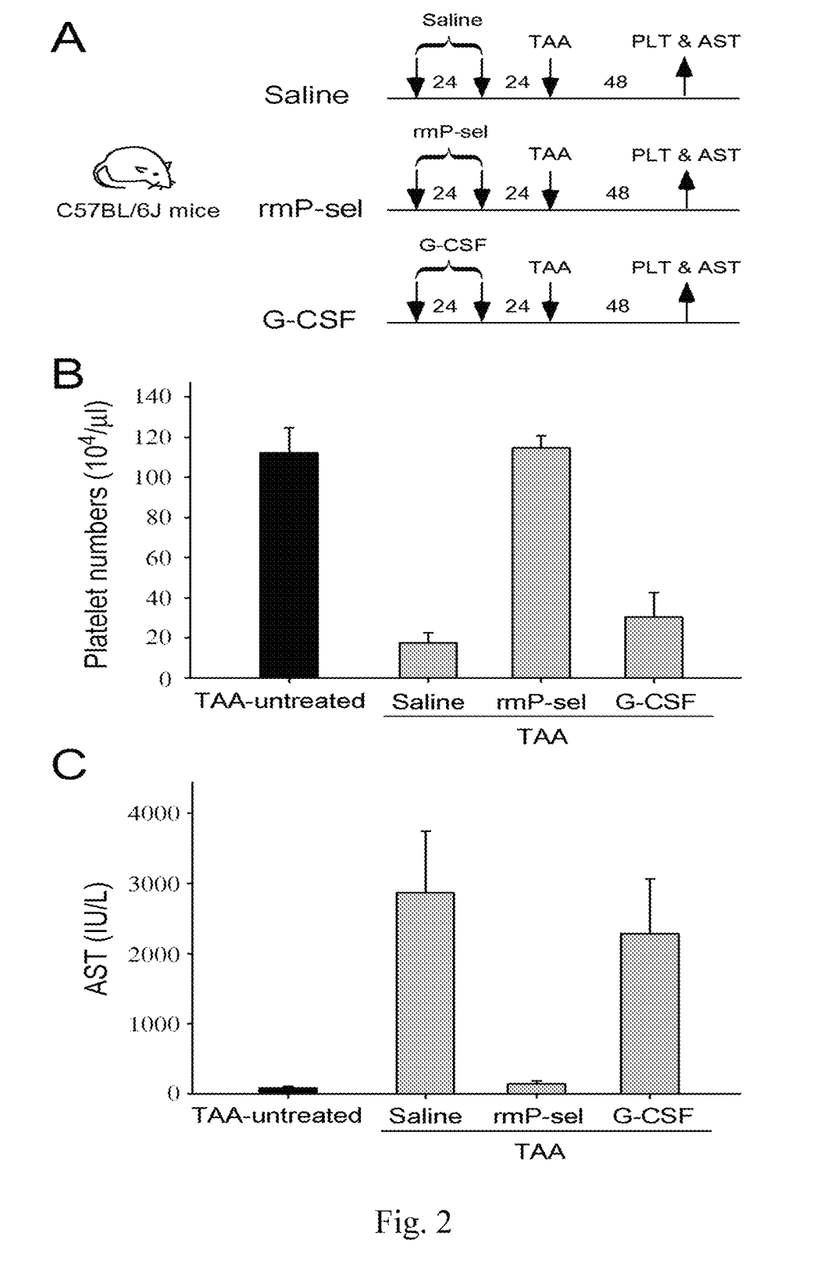
FIG. 2. Soluble P-selectin but not G-CSF treatments ameliorated thioacetamide (TAA)-induced thrombocytopenia and liver injury in mice. Recombinant mouse soluble P-selectin and G-CSF (Filgrastim®) (both 0.1 mg/kg body weight) were intravascular injected twice into 8-week-old experimental male C57Bl/6J mice in a 24 h interval; and hepatotoxic drug thrombocytopenia (TAA) was administrated with additional 24 h (A, outline). Platelet (PLT) counts (B) and circulating liver specific enzyme aspartate aminotransferase (AST) levels (C) were analyzed 48 h after TAA treatments, following previously described methods.

Example 2 Soluble P-Selectin Ameliorated Thioacetamide (TAA)-Induced Thrombocytopenia and Liver Injury C57BL/6J mice were injected with TAA to induce acute liver injury and then rescued with or without rm-Psel (FIG. 2A, time table). We found that pretreatment with twice of rmP-sel could rescue reduced-platelet counts in peripheral blood to normal level (FIG. 2B). Aspartate aminotransferase (AST) enzyme activity is a standard marker to measure liver injury. Data also revealed that rmP-sel ameliorated the liver damages (FIG. 2C). Our data suggested that rmP-sel treatments exert tissue protective effect to reduce TAA-induced injury (n=4; results with statistical significance, $P<0.05$ rmP-sel vs. saline).

Figure 3:
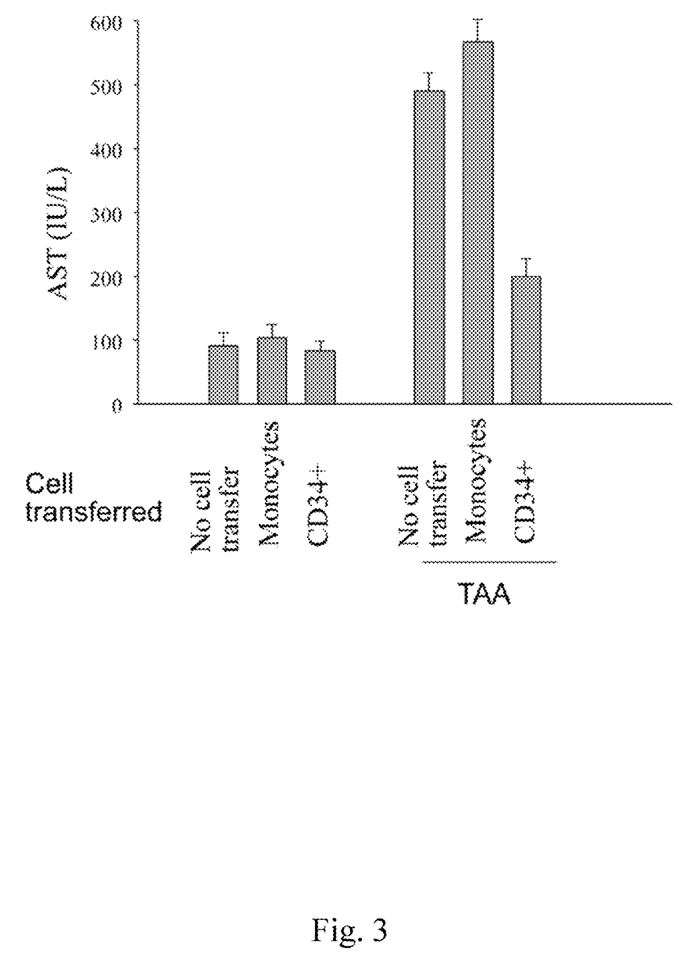
FIG. 3. Soluble P-selectin mobilized CD34+ cells are capable of rescuing thioacetamide (TAA)-induced liver damage. Following aforementioned method, soluble P-selectin mobilized CD34+ cells and peripheral blood mononuclear cells (PBMC; Monocytes) (both $5 \times 10^6$/mouse injection) were injected together with the TAA challenges (n=4; results with statistical significance, $P<0.05$ rmP-sel vs. the "no cell transfer" and the "monocyte" groups).

It has previously shown that stem cell treatments might have beneficial effects on the amelioration on the liver damages. To characterize whether rmP-Sel-elicited $CD34^+$ cells have tissue protective effect, we performed the adoptive transfer experiment. Our data showed that adoptive transfer of P-selectin-mobilized $CD34^+$ stem cells, but not peripheral blood mononuclear cells (PBMCs) is able to rescue TAA-induced hepatitis in mice (FIG. 3).

Figure 4:
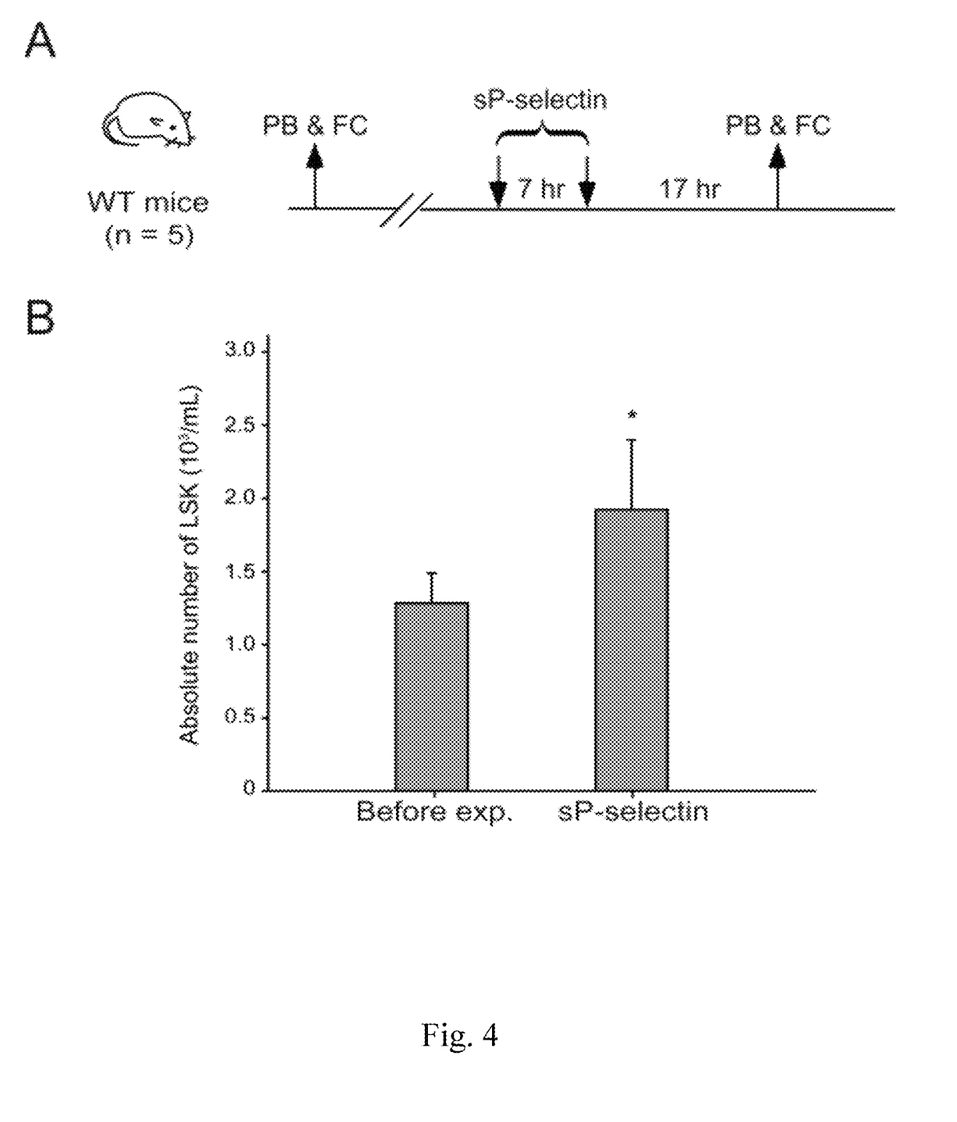
Figure 5:
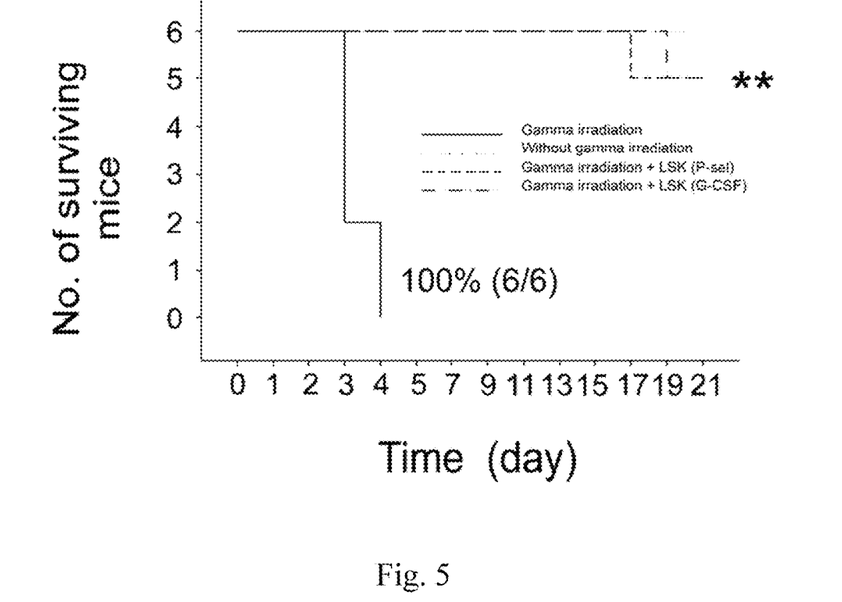
FIG. 5. P-selectin-mobilized LSK stem cells rescue the mortality of γ-irradiated mice, indicated the repopulation of bone marrow hematopoietic stem cells. C57BL/6J mice were subjected with or without a lethal dose γ-irradiation, which is used for bone marrow transplantation. Those γ-irradiated mice were further treated with vehicle, LSK stem cells that were obtained through P-selectin- or G-CSF-treatments mediated mobilization. Because both G-CSF and P-selectin-mobilized LSK stem cells can rescue the mortality of γ-irradiated mice, these results indicated the repopulation of bone marrow hematopoietic stem cells using both methods prepared LSK stem cells.

In human, G-CSF treatments mobilize $CD34^+$ stem cells, which are able to repopulate the γ-irradiated bone marrow. The LSK hematopoietic stem cell in mice is the cell lineage equivalent to the $CD34^+$ stem cell in human. To investigate the potential role of P-selectin-mobilized LSK cells in the repopulation of bone marrow, C57Bl/6 recipient mice that had received lethal irradiation with γ-ray were transplanted with $1\times10^5$ LSK cells mobilized with soluble P-selectin (FIG. 4) and G-CSF (FIG. 5). The engraftments are successfully transplanted as revealed by the rescue of 100% lethal γ-irradiation in mice (FIG. 5; 100% lethal in non-transplanted groups vs. approximately 83% survival of both soluble P-selectin mobilized LSK and G-CSF mobilized LSK groups).

Figure 6:
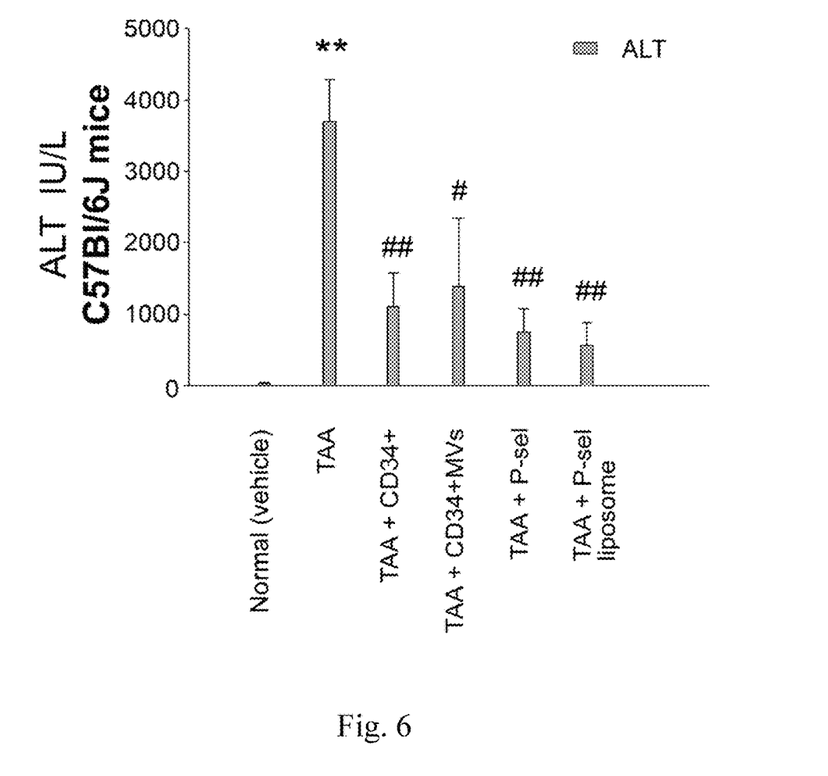
FIG. 6. P-selectin-mobilized CD34+ stem cell (PselMSCs), P-selectin mobilized CD34+ stem cell-derived microvesicles (PselSCMVs), soluble P-selectin and soluble P-selectin-conjugated liposome, on the amelioration of thioacetamide (TAA)-mediated liver damage. Treatments of PselMSCs and PselSCMVs, soluble P-selectin and soluble P-selectin-conjugated liposome, can rescue TAA mediated liver damages, as indicated by the circulating ALT, a liver-cell specifically expressed enzyme, levels. $**P<0.01$, vs. normal/vehicle groups; $\#P<0.05$, $\#\#P<0.01$, vs. TAA groups. n=6.

Protective role of PselMSCs and PselSCMVs, soluble P-selectin and soluble P-selectin-conjugated liposome were demonstrated using the TAA hepatitis mouse model. Treatments of PselMSCs and PselSCMVs, soluble P-selectin and soluble P-selectin-conjugated liposome markedly rescued TAA-induced elevation of high circulating alanine aminotransferase (ALT) levels in mice, suggesting that these reagents have ameliorative effects on TAA-induced liver damages (FIG. 6).

Figure 7:
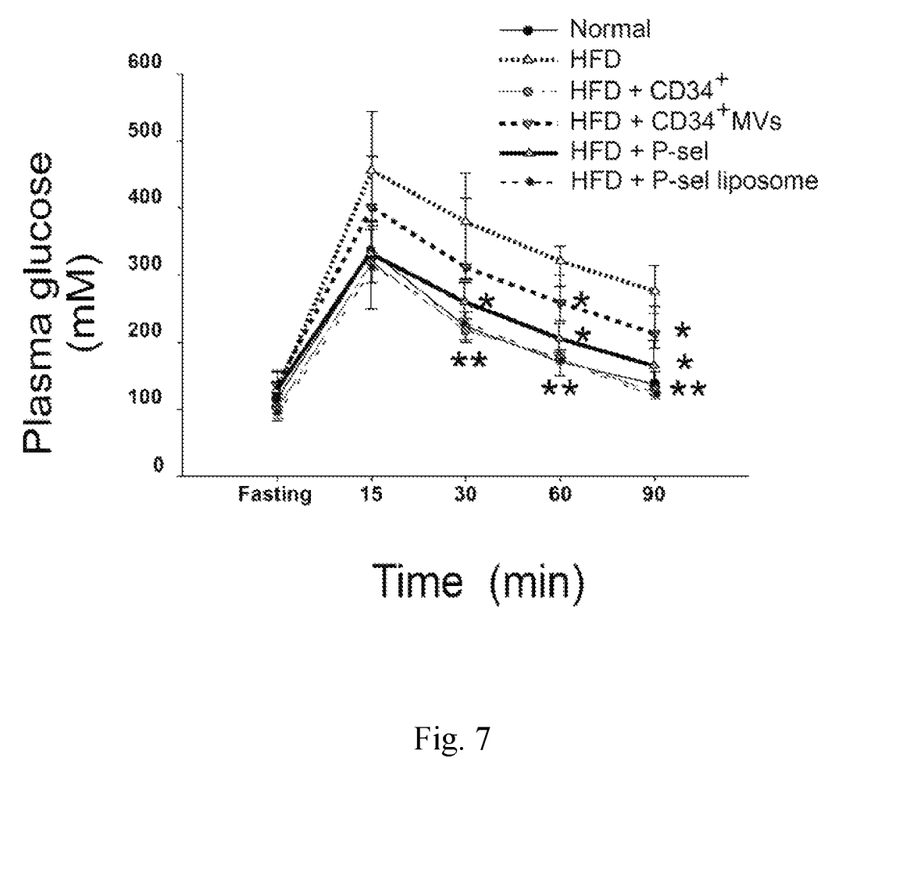
FIG. 7. Treatments of P-selectin-mobilized CD34+ stem cell (PselMSCs), P-selectin mobilized CD34+ stem cell-derived microvesicles (PselSCMVs), soluble P-selectin and soluble P-selectin-conjugated liposome, on the improvement of glucose tolerance in high fat diet (HFD)-induced diabetes mice. Glucose tolerance test (OGTT) experiment was performed, and the plasma glucose levels were determined in different experimental mouse groups. $*P<0.05$; $**P<0.01$, vs. respective HFD groups. n=6.

It is previously shown that adipose-derived mesenchymal stem cells may improve glucose homeostasis in high-fat diet-induced obese mice. However, whether PselMSCs, PselSCMVs, soluble P-selectin and soluble P-selectin-conjugated liposome remains elusive. Results of glucose tolerance (OGTT) analysis conclusively demonstrated that PselMSCs, PselSCMVs, soluble P-selectin and soluble P-selectin-conjugated liposomes all ameliorated high fat diet (HFD)-induced glucose resistant, whence reduce the blood glucose levels of HFD-mice (FIG. 7).

Figure 8:
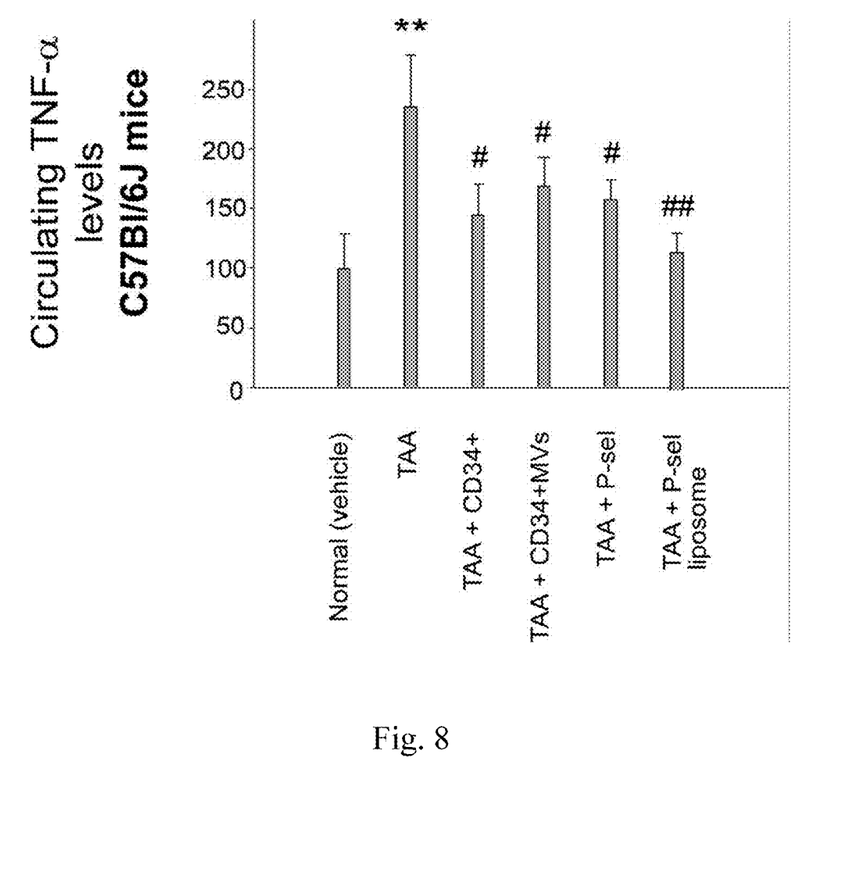
FIG. 8. Anti-inflammatory effects of P-selectin-mobilized CD34+ stem cell (PselMSCs), P-selectin mobilized CD34+ stem cell-derived microvesicles (PselSCMVs), soluble P-selectin and soluble P-selectin-conjugated liposome, on TAA-induced hepatitis in mice. The degree of TAA-induced inflammation was indicated by circulating TNF-α levels in mice; the averaged TNF-α level in normal/vehicle groups were normalized to 100%. $**P<0.01$, vs. normal/vehicle groups; $*P<0.05$, $**P<0.01$, vs. TAA groups. n=6.

Circulating TNF-α levels, which reveal the degree of inflammation, were analyzed in TAA-induced hepatitis mice. Data revealed that PselMSCs, PselSCMVs, soluble P-selectin and soluble P-selectin-conjugated liposomes all contain anti-inflammatory property, as treatments of these agents all markedly reduced TAA-induced induction of plasma TNF-α levels in mice (FIG. 8).

What is claimed is:

1. A method for ameliorating liver damage, improving glucose resistance, reducing TNF-α levels, inflammation, and hepatitis in a subject, comprising administering to the subject an effective amount of P-selectin mobilized circulating stem cells (PselMSCs) or P-selectin mobilized circulating stem cell-derived microvesicles (PselSCMVs).

2. The method of claim 1, wherein the P-selectin mobilized circulating stem cells are hematopoietic cells or bone marrow stem cells.

3. The method of claim 1, wherein the PselMSCs repopulate the bone marrow or hematopoietic stem cell population of the subject.

4. The method of claim 1, wherein the subject has TAA-induced liver damage, and administration of the PselMSCs or the PselSCMVs rescues thioacetamide (TAA)-induced elevation of high circulating alanine aminotransferase (ALT) levels to provide ameliorative effects on the TAA-induced liver damage, wherein the ALT levels are rescued by at least half compared to a control.

5. The method of claim 1, wherein the subject has high fat diet (HFD)-induced glucose resistance, and administration of the PselMSCs or the PselSCMVs ameliorates the HFD-induced glucose resistance.

6. The method of claim 1, wherein the subject has TAA-induced induction of plasma TNF-α levels, and administration of the PselMSCs or the PselSCMVs reduces the TAA-induced induction of plasma TNF-α levels.

* * * * *